United States Patent [19]

Howarth et al.

[11] Patent Number: 4,745,193
[45] Date of Patent: May 17, 1988

[54] PROCESS FOR THE PREPARATION OF FLUOROMETHYLPYRIDINES

[75] Inventors: Michael S. Howarth; Edward G. Scovell; David J. Watson, all of Lancashire, England

[73] Assignee: Imperial Chemical Industries PLC, London, England

[21] Appl. No.: 861,667

[22] Filed: May 9, 1986

Related U.S. Application Data

[63] Continuation of Ser. No. 564,200, Dec. 22, 1983, abandoned, which is a continuation of Ser. No. 366,350, Apr. 7, 1982, abandoned.

[30] Foreign Application Priority Data

Apr. 27, 1981 [GB] United Kingdom ............... 8112932

[51] Int. Cl.$^4$ ............................................. C07D 213/61
[52] U.S. Cl. ....................................... 546/345; 546/346
[58] Field of Search ................ 546/345, 346; 570/145, 570/147, 144

[56] References Cited

U.S. PATENT DOCUMENTS

| | | | |
|---|---|---|---|
| 3,388,174 | 6/1968 | Fielding et al. | 570/147 |
| 3,574,775 | 4/1971 | Fuller | 570/147 |
| 3,609,158 | 9/1971 | Torba | 546/302 |
| 4,031,100 | 6/1977 | Giacobbe | 546/345 |
| 4,071,521 | 1/1978 | Muench | 546/345 |
| 4,152,328 | 5/1979 | Nishiyama et al. | 546/345 X |
| 4,369,145 | 1/1983 | Soula | 570/147 X |
| 4,542,221 | 9/1985 | Jones | 546/345 |
| 4,547,577 | 10/1985 | Gatlin et al. | 546/346 X |
| 4,567,273 | 1/1986 | Fung | 546/346 X |
| 4,590,279 | 5/1986 | Fung et al. | 546/346 X |

FOREIGN PATENT DOCUMENTS

| | | |
|---|---|---|
| 0004434A2 | 10/1979 | European Pat. Off. |
| 0044890 | 2/1982 | European Pat. Off. |
| 2812607 | 4/1979 | Fed. Rep. of Germany |
| 1039987 | 8/1966 | United Kingdom |
| 1256082 | 12/1971 | United Kingdom |
| 2002368A | 2/1979 | United Kingdom |

OTHER PUBLICATIONS

Hudlicky, "Chemistry of Org. Fluorine Compounds", (1961), p. 89, Pergamon Press, N.Y.
Chambers et al.; J. Chem. Soc. (1964), pp. 3573-3574.
Finger et al.; J. Org. Chem., 28 (1963), pp. 1666-1668.
Banks et al.; J. Chem. Soc. (1965), pp. 594-595.
Maynard; J. Org. Chem., 28 (1963), pp. 112-115.
Ruhoff; Abstract of Ser. No. 779,219 filed 10-10-47.
A. Herstellung von Fluorverbindumgen, Houben-Weyl, Bd V/3, pp. 1 & 2, [no date available].

Primary Examiner—Joseph Paul Brust
Attorney, Agent, or Firm—Cushman, Darby & Cushman

[57] ABSTRACT

Fluoromethylpyridines of the formula:

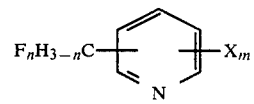

wherein the group $F_nH_{3-n}C-$ may be ortho, meta or para to the ring nitrogen atom, n is 1, 2 or 3, m is 1 to 4, X is Cl, Br, I or F and, when m is 2, 3 or 4 the substituents represented by X may be the same or different, at least one X being ortho or para to the $F_nH_{3-n}C-$ group, are prepared by reacting a compound of the formula:

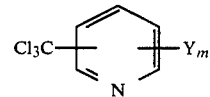

wherein Y is Cl, Br, I or F and m is 1 to 4, with potassium fluoride in a polar aprotic solvent under substantially anhydrous conditions. These fluoromethylpyridines are useful as intermediates for herbicides. 3,4,5-trifluoro-2-trifluoromethylpyridine and 2,6-difluoro-3-difluoromethylpyridine are novel compunds.

11 Claims, No Drawings

PROCESS FOR THE PREPARATION OF FLUOROMETHYLPYRIDINES

This is a continuation of application Ser. No. 564,200, filed 12/22/83, which was abandoned upon the filing hereof, which in turn is a continuation of Ser. No. 366,350 filed 4/7/82, now abandoned.

This invention relates to a chemical process and more particularly to a process for the preparation of certain fluoromethyl pyridines.

It is know to prepare 2-chloro-5-trifluoromethylpyridine by the reaction of hydrogen fluoride on 2chloro-5-trichloromethylpyridine, but this process if unattractive, particularly on the large scale, because of the hazards associated with the handling of hydrogen fluoride and the consequent necessity for special plant.

It is also known (see, for example, UK Patent Specification No. 1256082; J. Chem. Soc., 1964, 3573; J. Chem. Soc., 1965, 594) to react chloropyridines with potassium fluoride, in the presence or absence of a polar aprotic solvent, in order to replace chlorine by fluorine. However, it has not hitherto been known to replace chlorine by fluorine in side-chain chlorinated pyridines in this way.

According to the present invention there is provided a process for the preparation of fluoromethyl pyridines of formula (I):

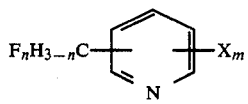

wherein the group $F_nH_{3-n}C-$ may be ortho, meta or para to the ring nitrogen atom, n is 1, 2 or 3, m is 1 to 4, X is Cl, Br, I or F and, when m is 2, 3 or 4 the substituents represented by X may be the same or different, at least one X being ortho or para to the $F_nH_{3-n}C-$ group, which comprises reacting a compound of formula (II):

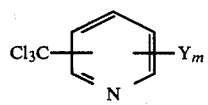

wherein Y is Cl, Br, I or F and m is 1 to 4 , with potassium fluoride in a polar aprotic solvent under substantially anhydrous conditions.

Examples of compounds of formula (II) which may be used as starting materials in the above process are 2-chloro-5-trichloromethylpyridine, 2-dichloro-3-trichloromethylpyridine, 3,4,5-trichloro-2-trichloromethylpyridine and 2,3-dichloro-5-trichloromethylpyridine.

Examples of the polar aprotic solvents which may be used are sulpholane, dimethylformamide and dimethyl acetamide.

It is preferred to used an excess of at least 25% over the theoretical quantity of potassium fluoride required to replace all of the non-fluorine halogen atoms in the compound of formula (II) by fluorine.

The amount of polar aprotic solvent which is used is not critical and is conveniently about 10 times the weight of compound of formual (II).

In order to ensure that the reaction conditions are anhydrous it is preferred to incorporate with the polar aprotic solvent a miscible co-solvent which is preferably capable of removing traces of water from the system by azeotropic distillation. Suitable co-solvents are hydrocarbons and halogenated hydrocarbons, for example, toluene, xylene, kerosene and the complex mixture of aromatic hydrocarbons, boiling point ca.164°–220° C., comprising approximately 70% by weight of isomeric trimethylbenzenes, the remainder consisting of other higher boiling aromatic compounds, which is sold by Imperial Chemical Industries PLC under the name 'AROMASOL H' (AROMASOL is a Registered Trade Mark). The use of such co-solvents also helps to suppress the formation of by-products.

It is necessary that the potassium fluoride should be in the right physical form, i.e. finely-divided, if the reaction is to proceed smoothly at an acceptable rate. Thus, the reaction is very sluggish if crystalline potassium fluoride is used. Amorphours or spray-dried potassium fluoride are particularly suitable. Satisfactory results are also obtained by milling the potassium fluoride in the polar aprotic solvent and using the resulting slurry. If desired, a minor amount of cesium fluoride may be used as a reaction promoter in admixtue with the potassium fluoride.

Reaction temperatures from 100° to 200° C., preferably 140° to 170° C., may be used.

The reaction is preferably conducted in the presence of a phase-transfer catalyst, for example, a tetraalkyl quaternary ammonium halide such as cetyl trimethylammonium bromide, tetrabutylammonium bromide, lauryltrimethylammonium bromide or benzyldimethyllauryl ammonium chloride. Yields are considerably lower in the absence of a phase transfer catalyst.

The process of the present invention, in addition to the surprising replacement of chlorine in trichloromethyl pyridines by fluorine when the trichloromethyl group has the relationship to the ring nitrogen atom of the pyridine nucleus and other nuclear halogen substituents specified in the statement of invention, also exhibits other features. Thus, whereas halogen atoms other than fluorine in the pyridine ring are generally replace by fluorine when the invention process is carried out, this is not aloways the case, and 2,3-dichloro-5-trichloromethylpyridine [(III); preparation: Published European Patent Application No. 4433] yields 3-chloro-2-fluoro-5-trifluoromethylpyridine [(IV); a known compound disclosed in Published European Patent Application No. 4414]

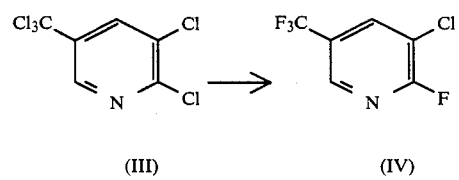

(III)　　　　　　　　(IV)

the chlorine in the 3-position remaining unchanged whilst all other chlorine atoms are replaced by fluroine.

When 2-chloro-5-trichloromethylpyridine (V) is the starting material in the invention process, three fluorinated products have been detected, as in the following scheme:

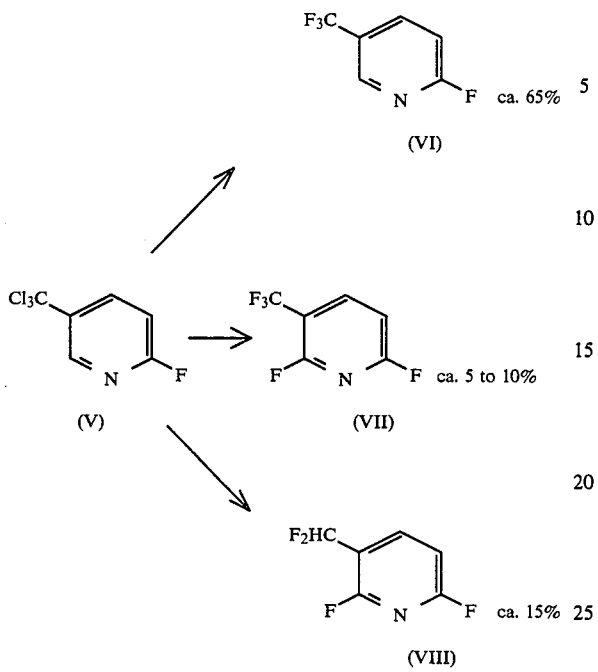

The expected product, 2-fluoro-5-trifluoromethyl-pyridine (VI) predominates, but significant quantities of the by-products 2,6-difluoro-5-trifluoromethylpyridine (VII) and 2,6-difluoro-3-difluoromethylpyridine (VIII) are also obtained.

The fluoromethylpyridines of formual (I) are useful as intermediates in the preparation of herbicides such as are described in, for example, European Patent Publication No. 1473. For this purpose it is not essential to isolate the compound from its solution in a polar aprotic solvent, since the latter is also a suitable solvent for carrying out certain stages in the herbicide preparation.

2-Chloro-5-trichloromethylpyridine which is one of the starting materials used in the present process is a known compound which may be prepared as described in European Patent Publication No. 1473 and U.S. Pat. No. 4,317,913.

2-Chloro-5-trichloromethylpyridine may also be prepared by a process which comprises the liquid-phase chlorination of 2-chloro-5-methylpyridine, 2-bromo-5-methylpyridine or their salts with hydrogen chloride or hydrogen bromide, in the presence of a chemical free-radical generator which may be any of those compounds which are known from the art and used in practice for such purposes, for example, azobisisobutyronitrile or benzoyl peroxide.

The amount of free-radical generator which is used may be from 0.001 to 1.0 mol per mole of the 2-chloro- (or bromo-)-5-methylpyridine or salt thereof which is used as starting material. It is convenient to add the total amount of free-radical generator in several protions during the course of the reaction.

The process may be carried out in the absence of a solvent, but it is preferred to use a solvent which is substantially inert to the reactants under the conditions of the reaction. Suitable solvents are, for example, carbon tetrachloride and monochlorobenzene.

Reaction temperatures from normal room temperature to 150° C. may be used.

The progress of the reaction may be followed by periodic gas chromatographic analysis of the reaction mixture, the chlorination being stopped when reaction is found to be substantially complete.

The reaction product may be recovered from the reaction mixture by conventional means. For example, excess chlorine may be removed from the reaction mixture by passing a stream of an inert gas such as nitrogen through the mixture, which may then be washed with water, followed by removal of the solvent by evaporation or distillation to give the crude product.

The 2-bromo-5-methylpyridine and 2-chloro-5-methylpyridine starting materials are known compounds. Their salts with hydrogen chloride or hydrogen bromide may be prepared, for example, by the action of the appropriate hydrogen halide gas on a solution or the pyridine derivative in an inert orgainc solvent.

2-Bromo- (or chloro-)-5-methylpyridine may themselves be prepared by a modification of the Craign process for the preparation of 2-bromopyridine from 2-aminopyridine.

L. C. Craig in J. Amer. Chem. Soc., 56, 231–232 (1934) describes a process for the preparation of 2-bromopyridine by diazotising 2-aminopyridine in hydrobromic acid solution in the presence of excess bromine. Under the optimum conditions discovered for this process there were used 5 mols of hydrobromic acid, 3 mols of bromine and 2.5 mols of sodium nitrite per mol of 2-aminopyridine, to give an 87% yield of 2-bromopyridine.

2-Bromo-5-methylpyridine may similarly be prepared by diazotising 2-amino-5-methylpyridine in hydrobromic acid solution in the presence of excess bromine.

Good yields of 2-bromo-5-methylpyridine are obtained by using 3 mols of hydrobromic acid, 2 mols of bromine and 1.5 mols of sodium nitrite per mol of 2-amino-5-methylpyridine. Under these conditions weight yields of product in excess of 95% may be obtained.

The process is conducted by dissolving the 2-aminopyridine in the hydrobromic acid (conveniently the commercially available concentrated hydrobromic acid containing 48% w/w hydrogen bromide), cooling the solution below 5° C., adding the bromine below 5° C., followed by the sodium nitrite as a strong aqueous solution added gradually during about 3 hours, again keeping the temperature below 5° C. The reaction mixture is then allowed to warm up to normal room temperature (conveniently overnight) and basified by the addition of aqueous sodium hydroxide solution until an alkaline reaction to Titan Yellow test paper is obtained, meanwhile keeping the temperature below 30° C. The basified reaction mixture is then extracted with a suitable water-immiscible organic solvent, for example, diethyl ether, dichloromethane or carbon tetrachloride, optionally after dilution with water, and the solvent is removed from the extract by distillation to give the desired product.

In a variant of the above process the relatively expensive hydrobromic acid may be replaced by hydrochloric acid. In this case it is convenient to use about 5 mols of hydrochloric acid, 1 mol of bromine and 2.5 mols of sodium nitrite per mol of 2-amino-5-methylpyridine, the reaction being conducted essentially as described previously. A mixture of 2-bromo- and 2-chloro-5-methylpyridine is obtained in acceptable yield.

2-Amino-5-methylpyridine, the starting material in the above process, is a commercially available product.

The invention is illustrated by the following Examples in which parts and percentages are by weight unless otherwise indicated, the relationship between parts by weight and parts by volume being that of the kilogram to the liter.

EXAMPLE 1

Anhydrous potassium fluoride (amorphous) (33.6 parts) slurried in sulpholane (tetrahydrothiophene-1,1-dioxide) (126 parts) and xylene (9.5 parts) was heated at 170° C. for 45 mintes under a flow of nitrogen in a flask set for azeotropic distillation. A trace of water and some xylene was distilled from the reactor. The temperature was reduced to 138° C. and the flask set for distillation to a receiver. 2-Chloro-5-trichloromethylpyridine (11.5 parts at 100%) was added and the temperature raised again to 170° C. The mixture was stirred at 170° C. for 17 hours in which time 13.26 parts of distillates were collected in the receiver. The distillates were shown by analysis to contain 2-fluoro-5-trifluoromethylpyridine corresponding to ca. 15% theory yield together with sulpholane, xylene and a trace of unreacted starting material.

EXAMPLE 2

Anhydrous potassium fluoride (amorphous) (33.6 parts) and cetyl trimethylammonium bromide (1 part) slurried in sulpholane (126 parts) and xylene (43.3 parts) was heated at 177° C. under a flow of nitrogen in a flask set for azeotropic distillation. 35 parts by volume of distillates containing a trace of water were removed from the reactor. The temperature was reduced to 138° C. and the flask set for total reflux. 2-Chloro-5-trichloromethylpyridine (11.5 parts at 100%) was added and the temperature raised to 159° C. in 1½ hours. The mixture was stirred at 159° C. for 1¼ hours when examination of a sample revealed the absence of starting material. The mixture was cooled under nitrogen and distilled under reduced pressure, collecting 12.9 parts of distillates b.p. 26°–31° C. at 13 mm Hg abs. The distillates were shown by analysis to contain ca 20% of 2-fluoro-5-trifluoromethylpyridine, corresponding to ca. 32% theory yield, together with sulpholane and xylene.

EXAMPLE 3

Anhydrous potassium fluoride (crystalline) (33.6 parts) was Silverson milled for 15 minutes in N,N-dimethyl acetamide (94.5 parts) to ensure a finely-divided physical form. The suspension was transferred to a flask containing cetyl trimethylammonium bromide (1 part) and xylene (43.3 parts). The mixture was stirred and heated to at 155° C., 30 parts by volume being removed by azeotropic distillation. The temperature was reduced to 137° C. and the flask set for total reflux. 2-Chloro-5-trichloromethylpyridine (11.5 parts at 100%) was added and the temperature raised to 143° C. The mixture was stirred at 143° C. for 17½ hours when examination of a sample revealed the absence of starting material. The mixture was cooled and distilled under reduced pressure, collecting 37.3 parts of distillates b.p. 28°–54° C. at 15 mm Hg.abs. The distillates were shown by analysis to contain ca 9% of 2-fluoro-5-trifluoromethylpyridine, corresponding to ca 40% theory yield. A further quantity of 2-fluoro-5-trifluoromethylpyridine estimates at 9% of the theory yield was identified in the still residue.

EXAMPLE 4

Anhydrous potassium fluoride (crystalline) (33.6 parts) was Silverson milled for 15 minutes in N,N-dimethylacetamide (94.5 parts) to ensure a finely-divided physical form. The suspension was transferred to a flask containing cetyl trimethylammonium bromide (1 part) followed by a wash of N,N-dimethylacetamide (20.8 parts). The flask was set for distillation to a receiver and the stirred mixture heated to distillation. Distillation was continued to a column-head temperature of 165° C. (kettle temperature 167° C.), 30 parts by volume of distillates being collected. The temperature was reduced to 142° C. under nitrogen and 2-chloro-5-trichloromethylpyridine (11.5 parts at 100%) was added. The mixture was stirred at 142° C. under nitrogen for 8 hours then cooled under nitrogen.

The supernatant liquors were analysed and the 2-fluoro-5-trifluoromethylpyridine content estimates at 6.4% corresponding to a 77% theory yield.

EXAMPLE 5

2.6-Dichloro-3-trichloromethylpyridine (40 g; 1 equiv.), dry potassium fluoride (130.7 g; 15 equiv.) and dry sulpholane (200 ml) were stirred together at 160° for 16 hours under gentle reflux. A further quantity of potassium fluoride (26.14 g; 2 equiv.) was then added, the reaction mixture was stirred for a further 3 hours at 160°–170° C., allowed to cool to room temperature and filtered from the inorganic residues into a chilled flask. The filter cake was washed with sulpholane and the combined filtrates were distilled to give 2.6-dichloro-3-trichloromethylpyridine as a colorless oil [17.0 g; b.p. 38°–43° C./24–27 mm Hg ($32-36 \times 10^{-3}$ bar)], the sulpholane remaining behind in the distillation vessel. Gas-liquid chromatographic (glc) analysis showed the product to be 95% pure, yield 58.6% of theoretical. 'H nmr (CDCl$_3$): Y 1.80 (q(J=7 Hz), 1H); 2.00 (dd(J=8 and 3 Hz), 1H). 'nmr and glc analysis of a mixture of the reaction product with authentic material showed complete coincidence.

The 2,6-dichloro-3-trichloromethylpyridine used as starting material in this example was obtained as described by Horn, Mutterer and Weis in Helv.Chim.Acta, 59, 190 (1976).

2,6-Difluoro-3-trifluoromethylpyridine is disclosed in Helv.Chim.Acta, 59, 230 (1976).

EXAMPLE 6

Potassium fluoride (32.675 g), sulpholane (50 ml) and toluene (25 ml) were subjected to azeotropic distillation (internal temperature 176° C.) to remove traces of moisture. 20 ml of distillate were collected. 2,6-Dichloro-3-trichloromethylpyridine (15.75 g) was added to the dry potassium fluoride slurry at 156° C. and the reaction mixture was stirred for 16 hours at 145°–150° C., followed by a further 20 hours at 160° C. After cooling, the reaction mixture was diluted with sulpholane and distilled to give 6 g of a distillate, b.p. 41°–47° C./22 mm Hg ($29 \times 10^{-3}$ bar). Glc analysis of the product indicates that it is a mixture of toluene and 2,6-difluoro-3-trifluoromethylpyridine.

EXAMPLE 7

Potassium fluoride (13.2 g), cetyl trimethylammonium bromide (1.3 g) and dimethyl acetamide (100 ml) were mixed together and dried by distillation until a constant column head temperature was obtained. 3,4,5-

Trichloro-2-trichloromethylpyridine (5.7 g) was added, the reaction mixture was heated for 16 hours at 125° C., then cooled and filtered. The filtrate was examined by glc and mass spectrometry. The results were consistent with the product being 3,4,5-trichloro-2-trichloromethylpyridine.

The 3,4,5-trichloro-2-trichloromethylpyridine used as starting material in this example was obtained.

EXAMPLE 8

This is a comparative Example and does not illustrate the process of the invention.

Potassium fluoride (21.75 g), cetyl trimethylammonium bromide (2 g) and dimethyl acetamide (150 ml) were mixed together and dried by distillation until a constant column head temperature was achieved, 45 ml of solvent being collected. 2,6-Dichloro-4-trichloromethylpyridine (13.3 g) was added, the reaction mixture was stirred for 18.75 hours at 120° C., then cooled and filtered. The filtrate was examined by glc and mass spectrometry. The results were consistent with the product being 2,6-difluoro-4-trichloromethylpyridine.

The 2,6-dichloro-4-trichloromethylpyridine used as starting material in this example is disclosed in U.S. Pat. No. 3,799,935.

EXAMPLE 9

Potassium fluoride (33.6 g), sulpholane (100 ml) and xylene (11 ml) were mixed together and dried by distillation until the internal temperature was 170° C. 2-Chloro-5-trichloromethylpyridine (12.2 g; 95% strength) was added at 138° C., the reaction mixture was heated at 170° C. for 17 hours and then distilled to give 13.26 g of distillate. Glc analysis of the latter indicated that approximately 15% of the theoretical yield of of toluene and 2,6-difluoro-3-trifluoromethylpyridine had been obtained.

EXAMPLE 10

The procedure described in Example 9 was repeated except that cetyl trimethylammonium bromide (1.0 g) was added with the potassium fluoride. A yield of 2-fluoro-5-trifluoromethylpyridine estimated at 32% of theoretical was obtained after 3 hours reaction at 146°–160° C.

EXAMPLE 11

The procedure described in Example 10 was repeated except thta the sulpholane was replaced by dimethyl acetamide. A yield of 2-fluoro-5-trifluoromethylpyridine estimated at 49% of theoretical was obtained after 17.5 hours reaction at 143° C.

EXAMPLE 12

Potassium fluoride (131 g), cetyl trimethylammonium bromide (6 g) and dimethylformamide (350 ml) were mixed together and dried by distilling until a constant column head temperature was achieved. After cooling below 100° C., 2-chloro-5-trichloromethylpyridine (78.3 g) was added, the reaction mixture was heated for 16 hours at 135° C., cooled and filtered. The yield of 2-fluoro-5-trifluoromethylpyridine in the filtrate was estimated by glc to be 72% of theoretical.

EXAMPLE 13

Potassium fluoride (145 g), cetyl trimethylammonium bromide (14 g) and dimethyl acetamide (350 ml) were mixed together and dried by distilling until a constant column head temperature was achieved. 2-Chloro-5-trichloromethylpyridine (78.3 g) was added, the reaction mixture was stirred at 118°–122° C. for 2 hours and the product was then distilled out during 9.5 hours at 200 mm Hg ($2.66 \times 10^{-1}$ bar), internal temperature 124° C. The yield of 2-fluoro-5-trifluoromethylpyridine was 66.8% of theoretical.

EXAMPLE 14

Potassium fluoride (580 g), cetyl trimethylammonium bromide (56 g) and dimethyl acetamide (1400 ml) were mixed together and dried by distilling under reduced pressure (170 mm Hg; $2.27 \times 10^{-1}$ bar) until a constant column head temperature was achieved. 188 g of distillate was collected.

The reaction vessel was set for distillation via a packed fractionation column, the internal temperature was adjusted to 130° C. and the pressure to 238 mm Hg ($3.17 \times 10^{-1}$ bar). Molten 2-chloro-5-trichloromethylpyridine (423.7 g at 92% strength) was then added at a steady rate during 4.5 hours. A reaction temperature of 125°–130° C. and a pressure of 230 mm Hg ($3.06 \times 10^{-1}$ bar) was then maintained for 1.75 hours, after which 2-fluoro-5-trifluoromethylpyridine was removed by fractional distillation during 16 hours. The yield of 2-fluoro-5-trifluoromethylpyridine was 66.3% of theoretical. It contained 4.3% of 2,6-difluoro-5-trifluoromethylpyridine and 11% of 2,6-difluoro-5-difluoromethylpyridine.

This mixture of products may be separated by first subjecting it to fractional distillation, whereby the more volatile 2-fluoro-5-trifluoromethylpyridine and 2,6-difluoro-5-trifluoromethylpyridine distil over, leaving behind the less volatile 2,6-difluoro-5-difluoromethylpyridine. The mixture of 2-fluoro-5-trifluoromethylpyridine is then dissolved in toluene to give an approximately 50% w/w solution, which is extracted with 63% w/w aqueous sulphuric acid solution, in which only the 2-fluoro-5-trifluoromethylpyridine dissolves. The sulphuric acid extract is diluted quickly to approximately 30% strength with water, when the 2-fluoro-5-trifluoromethylpyridine comes out of solution and can be extracted into toluene. It is necessary to conduct the extraction into 63% sulphuric acid and the subsequent dilution to 30% as quickly as possible, because the solution of 2-fluoro-5-trifluoromethylpyridine in 63% sulphuric acid is unstable, the product hydrolysing quite rapidly with consequent loss of yield.

EXAMPLE 15

Potassium fluoride (145 g), cetyl trimethylammonium bromide (14 g) and xylene (35 ml) were mixed together and dried by distilling under reduced pressure, 70 ml of distillate being collected.

Dimethyl acetamide (50 ml) and 2-chloro-5-trichloromethylpyridine (103.5 g at 93% strength) were added and the reaction mixture was heated at 120°–125° C. for 26 hours. The reaction vessel was set for distillation via a packed fractionation column and the contents were distilled under reduced pressure, thereby giving 2-fluoro-5-trifluoromethylpyridine in 55% yield as a solution in xylene.

EXAMPLE 16

The procedure described in Example 15 was repeated except that the quantities of xylene and dimethyl acetamide used were 286 ml and 114 ml respectively.

The yield of 2-fluoro-5-trifluoromethylpyridine was 68.2% of theoretical after 36 hours reaction at 124°–130° C.

EXAMPLE 17

The procedure described in Example 16 was repeated except that a high boiling petroleum fraction (boiling range 240°–260° C.) was used in place of xylene. The yield of 2-fluoro-5-trifluoromethylpyridine was 75% of theoretical.

EXAMPLE 18

This Example does not illustrate the process of the invention.

2-Amino-5-methylpyridine (54 parts) was dissolved in hydrobromic acid 48% (253 parts=121.5 parts at 100%), the solution was cooled to 5° C. and bromine (160 parts) was added below 5° C. A solution of sodium nitrite (51.75 parts) in water (75 parts) was added over approximately 3 hours maintaining the temperature below 5° C. throughout the addition. The flask contents were stirred and allowed to warm to room temperature overnight and were then basified by the addition of aqueous sodium hydroxide solution (317 parts) until they were alkaline to Titan Yellow test paper, the temperature being controlled below 30° C. Water (100 parts) and carbon tetrachloride (200 parts) were added, stirred at 25°–30° C. for 15 minutes and then allowed to settle and separate. The upper aqueous layer was extracted with carbon tetrachloride (200 parts). The combined carbon tetrachloride layers were concentrated by distilling to 80° C. under full water pump vacuum to yield a residue consisting essentially of 2-bromo-5-methylpyridine (82.5 parts)=95.9% on weight basis.

EXAMPLE 19

This Example does not illustrate the process of the invention.

2-Amino-5-methylpyridine (54 parts) and tetrabutylammonium bromide (0.5 part) were dissolved in hydrochloric acid 36° Tw (295 parts) the resultant solution was cooled to 5° C. and bromine (80 parts) was added maintaining the temperature below 5° C. Sodium nitrite (86.25 parts) was dissolved in water (125 parts) and the solution added over 5 hours to the other reactants which were maintained below 7° C. by cooling in an ice/salt bath. The preparation was then allowed to stir and warm to ambient temperature overnight, basified until alkaline to Titan Yellow test paper by the addition of aqueous sodium hydroxide solution and then extracted with methylene chloride (1×268 parts, 2×134 parts). The combined methylene chloride extracts were washed with water (200 parts) and then distilled, finally under reduced pressure, to yield a brown liquid (49.7 parts) containing 77.8% 2-chloro-5-methylpyridine and 19.2% 2-bromo-5-methylpyridine, i.e. a combined 2-chloro-, 2-bromo-5-methylpyridine, yield=67.0%.

EXAMPLE 20

This Example does not illustrate the process of the invention.

Preparation of 2-chloro-5-trichloromethylpyridine

2-Bromo-5-methylpyridine (40 parts) dissolved in carbon tetrachloride (500 parts) and water (10 parts) was heated to 70° C. with stirring, benzoyl peroxide 70% aqueous suspension (0.8 parts) was added and gaseous chlorine was passed in. Samples from the mixture were removed periodically and analysed by gas chromatography and the chlorine addition was stopped when conversion to 2-chloro-5-trichloromethylpyridine was seen to be substantially complete. After seven hours reaction time had elapsed a further portion of benzoyl peroxide 70% aqueous suspension (0.4 parts) was added and this was repeated at 14 hours. Time taken 20-25 hours. The mixture was then cooled and a stream of nitrogen passed through it for 60 minutes before being washed with water (4×400 ml) and evaporated to leave 54.8 parts of an oily residue which crystallised on standing. The residue was shown by analysis to contain 86.5% 2-chloro-5-trichloromethylpyridine corresponding to an 88.2% yield.

EXAMPLE 21

This Example does not illustrate the process of the invention.

Preparation of 2-chloro-5-trichloromethylpyridine

When the procedure of Example 1 is repeated with 2-chloro-5-methylpyridine (40 parts) in carbon tetrachloride (400 parts) with benzoyl peroxide 70% aqueous suspension (1.1 parts) [renewed after each seven hours reaction with 0.55 parts benzoyl peroxide 70% aqueous suspension], a yield of 75 parts product was obtained which was shown by analysis to contain 84.1% 2-chloro-5-trichloromethylpyridine, corresponding to a yield of 87.0%.

We claim:

1. A process for the preparation of fluoromethyl pyridines of the formula (I):

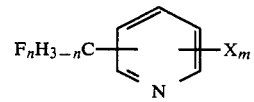

wherein the group $F_nH_{3-n}C-$ may be ortho, meta or para to the ring nitrogen atom, n is 1, 2, or 3, m is 1, 2 or 3, X is Cl or F and, when m is 2 or 3, the substituents represented by X may be the same or different, at least on X being ortho or para to the $F_nH_{3-n}C-$ group, which comprises reacting a mixture consisting essentially of a compound of formula (II):

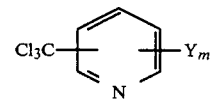

wherein Y is Cl or F and m is 1, 2 or 3 and potassium fluoride, alone or in the presence of a minor amount of cesium fluoride and, in either case, optionally in the presence of a phase transfer catalyst in a polar aprotic solvent under substantially anhydrous conditions.

2. A process as claimed in claim 1 wherein the compound of formula (II) is 2-chloro-5-trichloromethylpyridine and the product is a mixture of 2-fluoro-5-trifluoromethylpyridine, 2,6-difluoro-3-trifluoromethylpyridine and 2,6-difluoro-3-difluoromethylpyridine.

3. A process as claimed in claim 1 wherein the compound of formula (II) is 3,4,5-trichloro-2-trichloromethylpyridine and the product is 3,4,5-trifluoro-2-trifluoromethylpyridine.

4. A process as claimed in claim 1 wherein the compound of formula (II) is 2,3-dichloro-5-trichloromethylpyridine and the product is 3-chloro-2-fluoro-5-trifluoromethylpyridine.

5. A process as claimed in claim 1 or claim 2 or claim 3 or claim 4 wherein the potassium fluoride is in the finely divided form.

6. A process as claimed in claim 1 or claim 2 or claim 3 or claim 4 wherein the potassium fluoride is used in an excess of at least 25% over the theoretical quantity required to replace all of the non-fluorine halogen atoms in the compound of formula (II) by fluorine.

7. A process as claimed in claim 1 or claim 2 or claim 3 or claim 4 wherein there is incorporated with the polar aprotic solvent a miscible co-solvent capable of removing traces of water from the system by azeotropic distillation.

8. A process as claimed in claim 7 wherein the miscible co-solvent is a hydrocarbon or halogenated hydrocarbon.

9. A process as claimed in claim 1 or claim 2 or claim 3 or claim 4 wherein the reaction is conducted in the presence of a phase transfer catalyst.

10. A process as claimed in claim 9 wherein the phase transfer catalyst is a tetralkyl quaternary ammonium halide.

11. A process as set forth in claim 1 wherein n is 3 and X is fluorine.

* * * * *